United States Patent [19]

Krzaklewski et al.

[11] 3,957,042
[45] May 18, 1976

[54] SPATIAL INTRAUTERINE CONTRACEPTIVE INSERT

[75] Inventors: Stanislaw Krzaklewski; Andrzej Reszczynski, both of Wroclaw; Henryk Suski, Warsaw, all of Poland

[73] Assignee: Akademia Medyczna We Wroclawiu, Wrolaw, Poland

[22] Filed: Apr. 23, 1975

[21] Appl. No.: 570,794

[52] U.S. Cl. .......................... 128/130; 128/260
[51] Int. Cl.² .................... A61F 5/46; A61M 7/00
[58] Field of Search .................... 128/127–131, 128/260

[56] References Cited
UNITED STATES PATENTS

| | | | |
|---|---|---|---|
| 3,077,879 | 2/1963 | Knoch | 128/130 |
| 3,490,456 | 1/1970 | Kortum | 128/130 |
| 3,590,816 | 7/1971 | Rosenthal | 128/130 |
| 3,659,596 | 5/1972 | Robinson | 128/130 |

*Primary Examiner*—Lawrence W. Trapp
*Attorney, Agent, or Firm*—Haseltine, Lake & Waters

[57] ABSTRACT

A spatial intrauterine contraceptive insert which after being introduced by means of a normal inserter into the uterus cavity takes on by itself the appearance of a spatial body.

The insert has two arms 1, 2, the ends of which are connected permanently and formed into two spatial spirals along axes 4, 5 that intersect in an acute angle. In cross-section, the arms 1, 2 take on the shape of a circle. The parts of the arms 1, 2 which are formed as spirals of about 1½ turns have the appearance of a mirror image. Near the end of the first turn of the spiral the arms 1 and 2 are immobilized by means of a link 6 made of copper. At the juncture point of said arms there is provided a thread 7 for facilitating the removal of the insert from the uterus.

3 Claims, 3 Drawing Figures

SPATIAL INTRAUTERINE CONTRACEPTIVE INSERT

This invention relates to a spatial intrauterine contraceptive insert which constitutes an improvement in relation to the interuterine pesarium for contraception known from the applied formula No. 20 289 as well as the two armed intrauterine contraceptive insert disclosed in Polish Pat. No. 68,808.

The pesarium according to the formula No. 20 289 has a single trunk from which form two parted branches terminated with a non-coiling spiral; one of the branches is longer and its spiral is terminated with a thickening. The trunk and branches have a greater cross-section than those of the spirals.

The two-armed contraceptive insert according to Polish Pat. No. 68,808 has two non-coiling spirals, the individual branches of which are arranged in various planes; the intersection line determining the position of the trunk which integrates both branches into one whole.

The other of said solutions because of the use of two-layer spirals has an evident advantage over the previously known and applied Lippes loops, (U.S. Pat. No. 3,250,271) the form of double-"S" letter, the Otto ring in the form of a disk connected by radial ribs to the concentric ring, the single Margulies spiral provided with a leg that protrudes from the neck canal or the Birnberg pesarium in the shape of the letter "S" the common feature of which is a uniplanar arrangement of the contraceptive insert, facilitating a change in the position of the insert and its unintentional removal from the uterus cavity.

However all the hitherto known spirals except for the spiral according to Polish Pat. No. 68,808 feature uniplanar arrangements of the spiral and this does not ensure fully satisfactory contraceptive action and does not prevent the danger in the removal of the insert from the uterus cavity. The spiral according to Polish Pat. No. 68,808 partly eliminates the disadvantage of uniplanarity, but the object of the invention is the total elimination of said imperfection and the development of such an insert which after its introduction into the uterus cavity would each time by itself take the shape of a spatial kinetic body that would ensure steady elastic contact with the mucous membrane both of the front and rear uterus wall, regardless of the occurrence of possible muscle constriction of the uterus which can change the spatial arrangement of the uterus, while the technical problem to be solved is the development of a contraceptive insert capable of meeting this requirement.

This object has been attained by the utilization of the partly closed insert which for the purpose of preventing undesirable pregnancy is provided with two arms, the ends of which are connected permanently. They are then formed into two spirals along intersecting axes in an acute angle. Near the end of the first coil of each spiral, both arms are immobilized with respect to each other by means of a copper link.

The above-described design has a number of essential advantages. It provides a self-acting and reliable unfolding of both arms of the contraceptive insert in the uterus cavity, thus filling said uterus with the soft, flexible and rounded arms of the spiral. This increases the contact area of the insert with the mucous membrane of the uterus cavity thus considerably increasing the contraceptive efficiency of the insert as compared with flat or even two-layer inserts. Another advantage of the insert which results from its spatial form is its ability to firmly remain in the uterus cavity without falling out when employed by menstruating women or those affected by an insufficiency of internal tissue in the uterus neck which failure is frequently encountered.

The use of a thin ring of chemically pure copper as a link connecting the spiral arms provides copper ions, thus on one hand making for more efficient contraceptive action, while the other hand reduces the effects of a possible painful constriction of the uterus, which can occur.

The object of the invention is shown in the attached drawing in which

Figure 1:
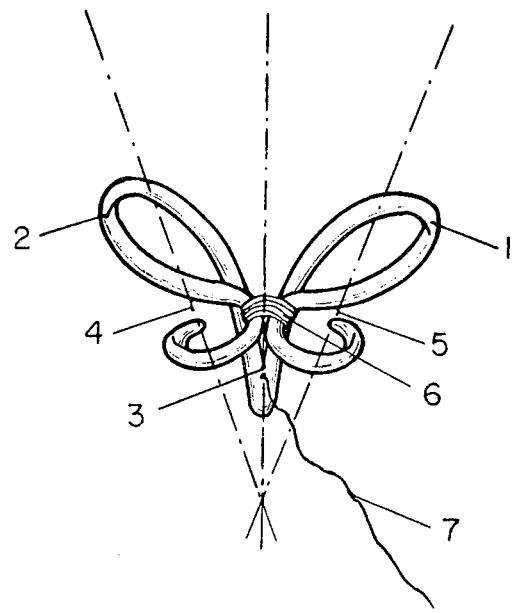
FIG. 1 shows the spatial intrauterine contraceptive insert seen from the front.
Figure 2:
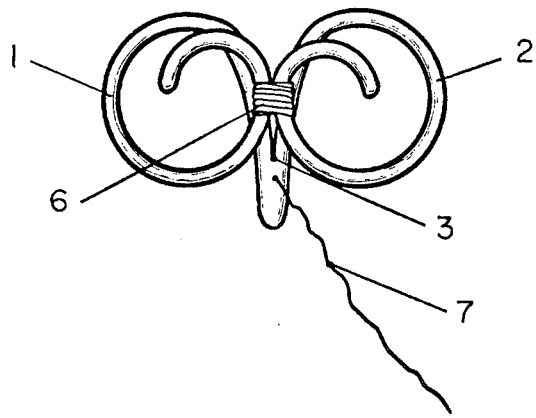
FIG. 2 shows the insert seen from the top.
Figure 3:
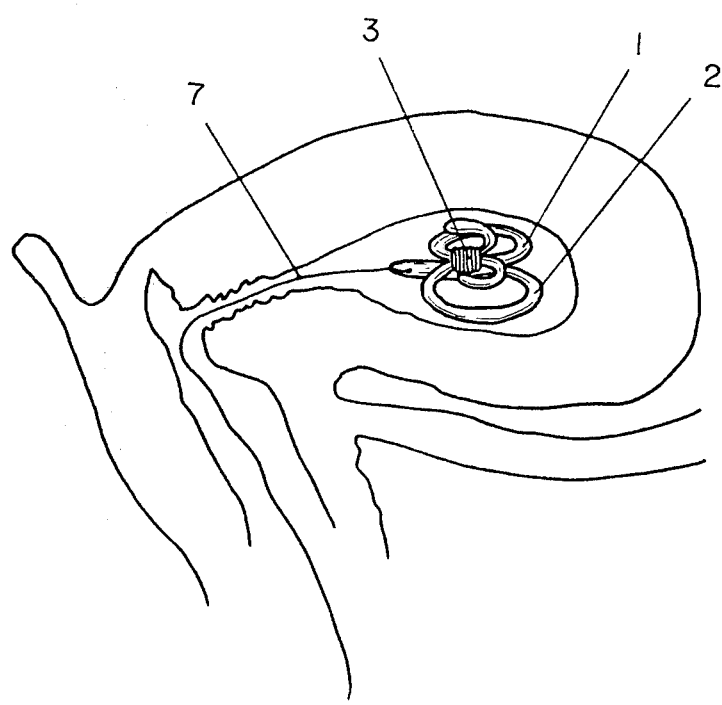
FIG. 3 shows in a side view the insert located in the uterus.

The contraceptive insert according to the invention has two arms 1, 2, the ends of which are connected permanently with one another at junction 3. These arms are then formed into two spatial spirals along axes 4 and 5 that intersect in an acute angle. In cross-section the arms 1 and 2 take a shape resembling a circle. The parts of the arms 1 and 2 which are formed as spirals have about a 1½ turn and have the appearance of a mirror images. Near the end of the first turn of the spiral, the arms 1 and 2 are immobilized by means of a link 6 made of copper. At juncture point 3 of said arms 1 and 2 there is provided a thin thread 7 facilitating the removal of the insert from the uterus.

To place the insert into the uterus, it is first disinfected and then introduced into the insertor. This is accomplished by pulling the thread 7 and thus for drawing both arms 1 and 2 of the spiral into the insertor tube. After preparing the patient for medical intervention and after performing following disinfection of the vagina with a gynaecological specula, the vagina is seized by means of a ballshaped instrument and the uterus neck is straightened by light stretching. The insertor is then placed into the neck canal and; by light movement of the piston causing the insert to push out of the uterus cavity. The properly introduced insert then returns by itself to the original spatial body shape and this can be easily determined after a self-acting pull-up of a certain length of the thread 7. Following removal of the piston from the insertor, the insertor tube is gently removed from the neck canal and any excess thread cut off. Should there be a necessity for removal of an insert, this can be done by means of surgical forceps grasping the projecting thread thus removing the insert from the uterus cavity.

We claim:

1. A spatial intrauterine contraceptive insert made of an elastic non-reactive plastic characterized by the feature of having two arms, the ends of which are connected permanently and formed into two spatial spirals along the axes that intersect in an acute angle, while near the end of the first loop of each spiral, both arms are immobilized by means of a link made of copper.

2. The insert according to claim 1, wherein said arms that are formed as spirals and situated along said axes have one and half loops and take on the appearance of mirror images.

3. The insert according to claim 1, wherein said arms in cross-section take on the shape of a circle.

* * * * *